United States Patent [19]

Eccli et al.

[11] Patent Number: 5,498,822
[45] Date of Patent: *Mar. 12, 1996

[54] SINGLE TEMPERATURE STAGE CRYSTALLIZATION OF PARAXYLENE

[75] Inventors: William D. Eccli, Princeton Junction, N.J.; Alexander D. S. Fremuth, Langhorne, Pa.

[73] Assignee: Mobil Oil Corporation, Fairfax, Va.

[*] Notice: The term of this patent shall not extend beyond the expiration date of Pat. No. 5,448,005.

[21] Appl. No.: 223,063

[22] Filed: Apr. 4, 1994

[51] Int. Cl.$^6$ .................................................. C07C 7/14
[52] U.S. Cl. ........................................ 585/816; 585/812
[58] Field of Search ................................ 585/812, 816

[56] References Cited

U.S. PATENT DOCUMENTS

| | | | |
|---|---|---|---|
| 2,541,682 | 2/1951 | Arnold | 260/674 |
| 2,766,309 | 10/1956 | Speed et al. | 585/816 |
| 3,462,509 | 8/1969 | Dresser et al. | 585/812 |
| 3,662,013 | 5/1972 | Machell et al. | 260/647 A |
| 3,720,647 | 3/1973 | Gelbe et al. | 585/816 |
| 3,723,558 | 3/1973 | Kramer | 260/674 A |
| 4,851,604 | 7/1989 | Absil et al. | 585/475 |
| 5,173,461 | 12/1992 | Absil et al. | 502/62 |
| 5,243,117 | 9/1993 | Chang et al. | 585/467 |
| 5,448,005 | 9/1995 | Eccli et al. | 585/812 |

FOREIGN PATENT DOCUMENTS

WO93/17788  9/1993  WIPO.

Primary Examiner—Sharon Gibson
Attorney, Agent, or Firm—Alexander J. McKillop; Dennis P. Santini; Lori F. Cuomo

[57] ABSTRACT

This invention is a crystallization process for p-xylene recovery. A single temperature crystallization stage is used for producing p-xylene from a feed having an above equilibrium p-xylene concentration, such as from toluene disproportionation.

10 Claims, 1 Drawing Sheet

SINGLE TEMPERATURE STAGE CRYSTALLIZATION OF PARAXYLENE

CROSS-REFERENCE TO RELATED APPLICATIONS

This application is related by subject matter to Ser. No. 08/222,730, filed concurrently herewith.

FIELD OF THE INVENTION

The process of the present invention relates to a process for the crystallization of a feed having a high paraxylene concentration.

BACKGROUND

Crystallization methods can be used to separate paraxylene (p-xylene) from a $C_8$ aromatic starting material which contains ethylbenzene, as well as the three xylene isomers. Use is made of the fact that the melting point of the individual $C_8$ isomers have significant temperature differences. P-xylene has a freezing point of 13.3° C., metaxylene has a freezing point of −47.9° C. and orthoxylene has a freezing point of −25.2° C. However, conventional crystallization methods can be used to make p-xylene with a purity of over 99.5 wt. % only with great expense.

Crystallization processes to recover p-xylene from a mixture of $C_8$ aromatics requires cooling the equilibrium feed mixture from reformate or xylene isomerization processes. Because it's melting point is much higher than that of the other $C_8$ aromatics, p-xylene is readily separated in the crystallizer after refrigeration of the stream. In conventional p-xylene crystallization processes, the feed contains about 22 to about 23 wt. % p-xylene. In order to crystallize out most of the p-xylene from solution, the feed has to be cooled to as low as about −85° to −95° F. Conventional crystallization processes operate in the manner described in U.S. Pat. No. 3,662,013.

In conventional crystallization the maximum theoretical p-xylene recovery is fixed by the temperature of the coldest crystallizer in the crystallization unit. That temperature is limited by eutectic temperature, the temperature at which a second component, generally m-xylene, starts to crystallize and contaminates the p-xylene crystals. Given an equilibrium mixture of xylenes in the crystallizer feed, the coldest crystallizer is cooled to within 5°–10° F. of the eutectic temperature to maximize p-xylene recovery. Theoretically, the p-xylene recovery is limited to about 70% at the eutectic temperature. P-xylene recoveries of 60–65% are typical.

In a conventional two stage crystallizer. Equilibrium $C_8$ aromatic feed is cooled to about −30° to −40° F. and mixed with second stage filtrate and then crystallized in a number of crystallizers in series, each crystallizer cooling the feed further, the coldest of which runs typically at about −80° to −90° F. The slurry solids and liquor, i.e. mother liquor, are separated by centrifuge. In the first stage, the solids become a wet cake with voids filled by the liquid containing only about 8–12 wt. % p-xylene. This low p-xylene liquid contaminates the crystals by 5–15%, depending on the drying efficiency of the centrifuge and prevents the p-xylene concentration from achieving the required 99.5+ wt. % purity. The remaining liquid is discharged as reject filtrate. This wet cake is either fully or partially melted and recrystallized or washed to remove the contaminants to achieve the required high p-xylene purity.

The second stage re-crystallizes the first stage product and filtrate p-xylene from the second stage recycle filtrate out of solution. The resulting slurry of crystals and mother liquor is centrifuged. The wet p-xylene crystals cake goes to the wash step, the remaining liquid is recycled filtrate. A controlled amount of the recycle filtrate is used to dilute the first stage product in order to control the slurry solids loading in the crystallizer. Typical centrifuges separate a slurry mixture containing no more than 35–45 wt. % solids. The second stage crystallizer operates at 0° to 40° F. and thus requires and processes a much smaller stream than the first stage and thus requires much less refrigeration.

The second stage cake voids are filled with liquid that is already rich in p-xylene, typically about 60–75 wt. %, and thus washing the crystals with product p-xylene can achieve a feed purity in the order of 99.5+ wt. % p-xylene.

A new approach to crystallization of p-xylene has now been found when processing a feed rich in p-xylene. It is an object of the present invention to provide an process for recovering p-xylene having a purity of at least 99.5 wt. % and preferably 99.8 wt. % from a feed rich in p-xylene.

SUMMARY OF THE INVENTION

It is believed that at a given a crystallizer temperature, as the p-xylene feed concentration increases, the p-xylene recovery increases. It is further believed that at a desired p-xylene recovery, as the feed concentration increases, the crystallizer temperature required to achieve this p-xylene recovery may be increased. Thus, at a fixed p-xylene feed concentration, as crystallizer temperature declines, p-xylene recovery increases.

With high enough p-xylene concentrations in the feed, the eutectic temperature is not a factor in the operation of the crystallizers of the present invention because cooling to the eutectic temperature is not required to get high p-xylene recovery rates. Achievable p-xylene purity of at least 99.5 wt. % can be achieved in a single temperature stage because of the high concentration of p-xylene in the feed and the high p-xylene concentration in the mother liquor.

The single temperature stage crystallizer of the present invention employs a wash using p-xylene product. No other type of wash, such as toluene, is needed to produce 99.5 wt. % p-xylene purity. The p-xylene product of the present invention requires no further processing.

The invention therefore includes a single stage crystallization process to recover p-xylene from a feed rich in p-xylene which comprises:

contacting said feed rich in p-xylene in a single temperature crystallization stage at a temperature in the range of from about −20° F. to about 50° F.;

withdrawing a slurry comprising p-xylene crystals from said single temperature crystallization stage;

passing said slurry to a separation means to form a cake and washing said cake with p-xylene;

passing said cake to a melt drum to form p-xylene product and withdrawing said p-xylene product;

recycling a portion of reject filtrate from said separation means to said single temperature crystallization stage; and withdrawing the remaining reject filtrate as mother liquor product.

DETAILED DESCRIPTION OF THE INVENTION

Figure 1:
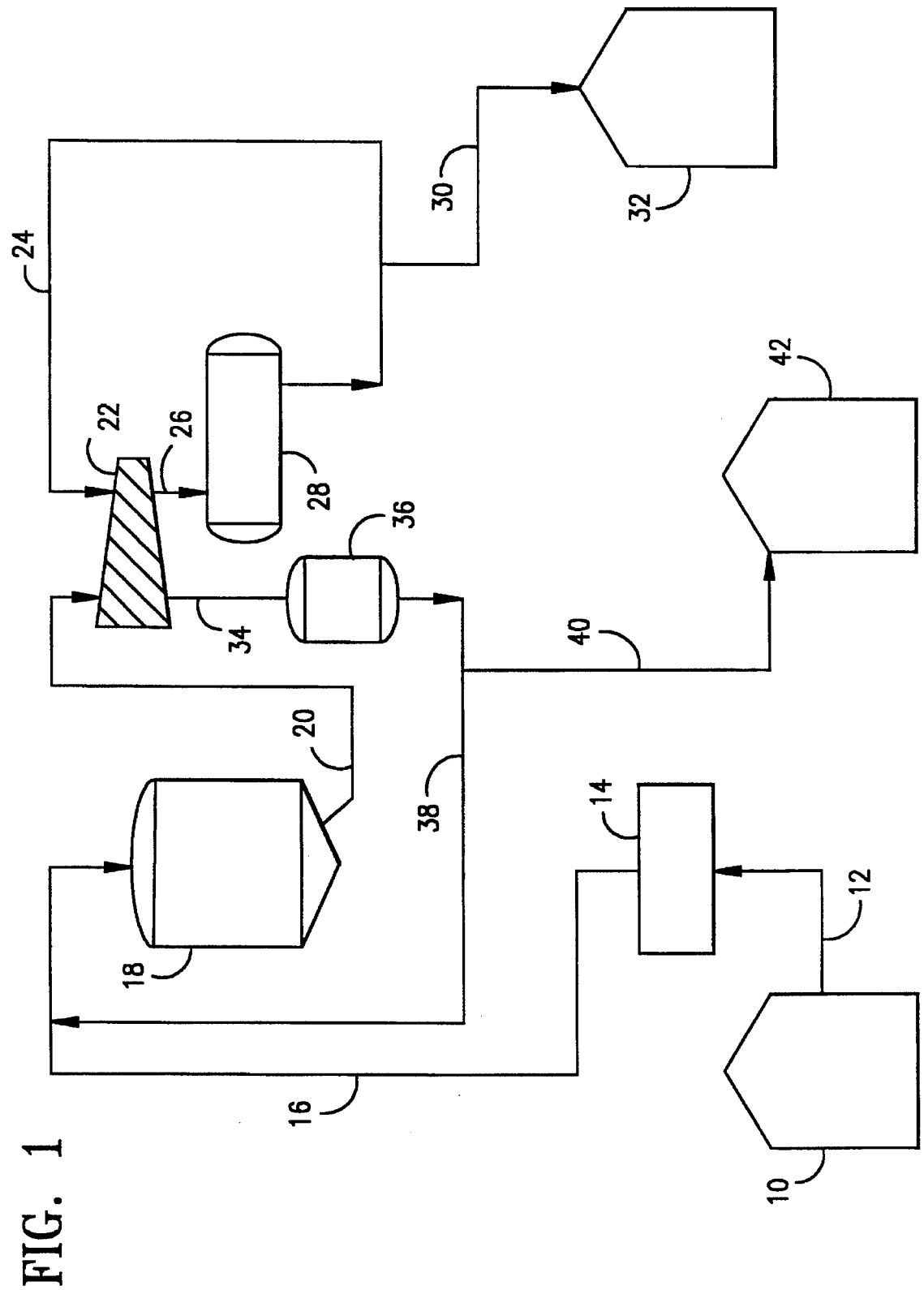
FIG. 1 is a simplified schematic diagram showing the process of the present invention.

The process of the present invention uses a high wt. % p-xylene feedstock, comprising at least about 97 wt. % p-xylene.

Suitable feedstocks with high p-xylene concentration include products of processes for the selective disproportionation of toluene to p-xylene using a silica-modified catalyst, such as those described in U.S. Pat. Nos. 4,851,604; 5,173,461; 5,243,117; and WO 93/17788, incorporated herein in their entirety by reference. Different p-xylene concentration feeds may also be combined and may be used as the high p-xylene concentration feedstock of the present invention.

In the process of the present invention, p-xylene rich feed enters a single temperature crystallization stage from which high purity p-xylene product is produced. The crystallization process of the present invention results in over about 80% recovery and preferably 90% recovery to a purity above about 99.5 wt. % and preferably 99.8 wt. % p-xylenes.

The process includes a crystallization stage operated at a temperature in the range of from about −20° F. to about 50° F. and preferably in the range of from about 20° F. to about 40° F., where high purity p-xylene is withdrawn.

The single temperature crystallization stage is typically operated at a pressure in the range of from about 20 psia to about 30 psia. The single temperature crystallization stage is typically sized for a residence time in the range of from about 3 to about 8 hours and more typically in the range of from about 4 to about 6 hours.

The process of the present invention uses a single stage refrigeration system to cool the process to the desired temperature. Propane or propylene can be used as the refrigerant for the single refrigeration stage. The temperature of the crystallization stage may be lowered to −20° F. without having to use a two stage refrigeration system if the desired p-xylene purity specifications can be met.

The continuous process of the present invention is illustrated in FIG. 1. A suitable p-xylene containing feed from feed tank 10 is passed through line 12 to heat exchanger 14 where it is initially cooled. The cooled feed is then passed through line 16 to a single temperature crystallization stage 18. The single temperature crystallization stage comprises one or more crystallizer vessels operated in series. In the single temperature crystallization stage, the feed is cooled to a temperature at which p-xylene crystallizes without crystallization of other xylene isomers in the feed. This temperature is dependent on the amounts of various components in the feed.

Slurry from the single temperature crystallization stage is withdrawn through line 20 and passed to a centrifuge separation means 22. Alternatively, a filter or hydrocyclone may be used for separation. The centrifuged cake is washed with recycled p-xylene product. The washed cake is passed through line 26 and melted in melt drum 28. A portion of p-xylene product is recycled as wash liquor through line 24. The remaining p-xylene product is passed through line 30 to storage tank 32. The reject filtrate, i.e. mother liquor, from the single temperature crystallization stage and reject p-xylene wash from centrifuge 22 are passed through line 34 to filtrate tank 36. A portion of the reject filtrate passes through line 40 to storage tank 42. The remaining reject filtrate is combined with the fresh feed to the single temperature crystallization stage through line 38.

The p-xylene concentration of the reject filtrate is generally in the range of from about 30 wt. % at −20° F. to about 80 wt. % at 40° F. The portion of the reject filtrate recycled to the single temperature crystallization stage is dependent on both the operating temperature and the solids concentration of the p-xylene slurry.

The following examples illustrate the process of the present invention.

EXAMPLE 1

A product from an MTPX process as set forth in U.S. Pat. No. 4,851,604, incorporated herein in its entirety by reference, is used as feed to the single temperature crystallization process of the present invention. The $C_8$ aromatics product contains p-xylene in an amount of about 97 wt. % of all $C_8$ aromatics. The $C_8$ aromatics are recovered and sent to a single temperature crystallization stage as shown in FIG. 1.

Three runs are conducted at temperatures ranging from 20° to 40° F. to produce a p-xylene product having a purity of >99.5 wt. % p-xylene. For Run 1, the single temperature crystallization stage is operated at a temperature of about 20°, resulting in a 92% recovery of p-xylene. For Run 2, the single temperature crystallization stage is operated at 35° F., resulting in a 88% recovery of p-xylene. For Run 3, the single temperature crystallization stage is operated at 40° F., resulting in a 80% recovery of p-xylene. In Run 3, the purity of the p-xylene recovered from the melt drum is >99.9 wt. %.

Changes and modifications in the specifically described embodiments can be carried out without departing from the scope of the invention which is intended to be limited only by the scope of the appended claims.

We claim:

1. A single temperature crystallization process to recover p-xylene from a feed rich in p-xylene which comprises:

contacting said feed rich in p-xylene in a single temperature crystallization stage at a temperature in the range of from about −20° to about 50° F.;

withdrawing a slurry comprising p-xylene crystals from said single temperature crystallization stage;

passing said slurry to a separation means to form a cake and washing said cake with p-xylene;

passing said cake to a melt drum to form p-xylene product and withdrawing said p-xylene product;

recycling a portion of reject filtrate from said separation means to said single temperature crystallization stage; and withdrawing the remaining reject filtrate as mother liquor product, wherein said feed rich in p-xylene comprises at least about 97 wt. % p-xylene.

2. The process according to claim 1 wherein said single temperature crystallization stage is operated at a temperature in the range of from about 20° F. to about 40° F.

3. The process according to claim 1 wherein the withdrawn p-xylene product has at least about a 99.5 wt. % p-xylene product purity.

4. The process according to claim 1 wherein the withdrawn p-xylene product has at least about an 99.8 wt. % p-xylene product purity.

5. The process according to claim 1 wherein said cake is washed with recycled p-xylene product from said melt drum.

6. The process according to claim 1 wherein said separation means comprises a centrifuge.

7. The process according to claim 1 wherein said feed is a product of toluene disproportionation using a silica-modified catalyst.

8. The process according to claim 1 wherein over 80% of the p-xylene in said feed is recovered.

9. The process according to claim 1 wherein over 90% p-xylene in said feed is recovered.

10. The process according to claim 1 wherein said single temperature crystallization stage is operated at a pressure in the range of from about 20 to about 30 psia.

* * * * *